United States Patent
Anba et al.

(10) Patent No.: US 7,241,610 B2
(45) Date of Patent: Jul. 10, 2007

(54) LACTIC ACID BACTERIA OVERPRODUCING EXOPOLYSACCHARIDES

(75) Inventors: Jamila Anba, Montigny-le-Bretonneaux (FR); Juliette Hagege, Orsay (FR); Stephane Chaillou, Antony (FR); Pierre Renault, Montigny-le-Bretonneaux (FR); Iris Besancon-Yoshpe, Magny-les-Hameaux (FR); Jerome Mengaud, Paris (FR); Christophe Fremaux, Poitiers (FR)

(73) Assignee: Institut National de la Recherche Agronomique (Inra), Paris (FR)

( * ) Notice: Subject to any disclaimer, the term of this patent is extended or adjusted under 35 U.S.C. 154(b) by 0 days.

(21) Appl. No.: 10/257,737

(22) PCT Filed: Apr. 18, 2001

(86) PCT No.: PCT/FR01/01198
§ 371 (c)(1),
(2), (4) Date: Dec. 3, 2004

(87) PCT Pub. No.: WO01/79476
PCT Pub. Date: Oct. 25, 2001

(65) Prior Publication Data
US 2005/0164354 A1 Jul. 28, 2005

(30) Foreign Application Priority Data
Apr. 18, 2000 (FR) ................................. 00 04971

(51) Int. Cl.
C12N 1/20 (2006.01)
C12N 15/70 (2006.01)
C12N 1/21 (2006.01)
C12N 9/24 (2006.01)
C12P 19/04 (2006.01)
C12P 21/06 (2006.01)
C07H 21/04 (2006.01)

(52) U.S. Cl. ................ 435/252.1; 435/252.3; 435/233; 435/69.1; 435/200; 435/320.1; 435/253.4; 435/183; 435/101; 536/23.2

(58) Field of Classification Search ................. 435/101, 435/23.2, 252.3
See application file for complete search history.

(56) References Cited
FOREIGN PATENT DOCUMENTS
WO  WO 98 18931 A  5/1998
WO  WO 01 49721 A  7/2001

OTHER PUBLICATIONS

Degeest et al. "Correlation of activities of the enzymes alpha-phosphoglucomutase, UDP-galactose 4-epimerase, and UDP-glucose pyrophosphorylase with exopolysaccharide biosynthesis by Streptococcus - - - ", Appl Environ Microbiol. Aug. 2000;66(8): 3519-3527.*

"Enzymes involved in carbohydrate metabolism and their role on exopolysaccharide production in *Streptococcus thermophilus*"; Journal of Applied Microbiology; Jan. 1998; pp. 108-114; XP000978853; Issue No. 1364-5072.

De Vuyst Luc et al; "Heteropolysaccharides from lactic acid bacteria"; FEMS Microbiology Reviews; Apr. 1999; pp. 153-177; XPOOO971896; Issue No. 0168-6445.

Kleerebezem Michiel et al; "Exopolysaccharides produced by *Lactococcus lactis*: From genetic engineering to improved rheological properties?."; Antonie Van Leeuwenhoek; Jul. 1999; pp. 357-365; XPOOO971897; Issue No. 0003-6072.

Hardy Gail G et al; "Capsule biosynthesis and basis metabolism in *Streptococcus pneumoniae* are linked through the cellular phosphoglucomutase"; Journal of Bacteriology; Apr. 2000; pp. 1854-1863; Issue No. 0021-9193.

Mollerach Marta et al; "characterization of the galU gene of *Streptococcus pneumoniae* encoding a uridine diphosphoglucose pyrophosphorylase: A gene essential for capsular polysaccharide biosynthesis"; Journal of Experimental Medicine; Dec. 7, 1998; pp. 2047-2056; XPOO2157671; Issue No. 0022-1007.

Glanzmann P et al; "*Staphylococcus aureus* argl, glmM genes and ORF1 and ORF2"; Database EMBL; Nov. 17, 1998; XPOO2175636.

Levander Fredrik et al; "Requirement for phosphoglucomutase in exopolysaccharide biosynthesis in glucose- and lactose-utilizing *Streptococcus thermophilus*"; Applied and Environmental Microbiology; Jun. 2001; pp. 2734-2738; XPOO1016100; Issue No. 0099-2240.

* cited by examiner

*Primary Examiner*—Rebecca E. Prouty
*Assistant Examiner*—Iqbal Chowdhury
(74) *Attorney, Agent, or Firm*—Alston & Bird LLP (57) ABSTRACT

The invention concerns lactic acid bacteria overproducing exopolysaccharides following mutation in the gene coding for α-phosphoglucomutase. Said mutants are useful, in particular for preparing fermented products or for producing exopolysaccharides.

5 Claims, 4 Drawing Sheets

ID NO: 2, and also any fragment of more than
LACTIC ACID BACTERIA OVERPRODUCING EXOPOLYSACCHARIDES The invention relates to the regulation of exocellular heteropolysaccharide production by lactic acid bacteria.

In general, polysaccharides are used a great deal as additives in food, but also in cosmetics and pharmaceutical products, for example as thickeners and/or gelling agents, texture stabilizers, fat substitutes, etc. Among the polysaccharides used in this way, mention will in particular be made of those produced by microorganisms, in particular bacteria, such as dextrans, xanthans, gellans, pullulans, etc.

Many species of lactic acid bacteria, in particular of *lactococci*, such as *Lactococcus lactis*, of *leuconostocs*, such as *Leuconostoc mesenteroide*, of *streptococci*, such as *Streptococcus thermophilus*, and of *lactobacilli*, such as *Lactobacillus casei*, *Lactobacillus sake*, *Lactobacillus rhamnosus*, *Lactobacillus acidophilus*, *Lactobacillus delbrueckii* subsp. *bulgaricus* and *Lactobacillus helveticus*, etc., produce polysaccharides.

These polysaccharides can be grouped into 2 categories: homopolysaccharides, such as dextrans, which result from the polymerization of a single sugar, and heteropolysaccharides, which have a complex structure, combining basic units consisting of two or more different sugars (commonly D-galactose, D-glucose and L-rhamnose).

The heteropolysaccharides of lactic acid bacteria are conventionally designated under the general term EPS (for exopolysaccharides), which will also be used hereinafter. They play a major role in the development of the texture, of the mouthfeel and of the rheology of fermented dairy products. In addition, it has been observed that some of them have biological activities by which they might exert diverse effects beneficial to the health [for review, cf. DE VUYST and DEGEEST, FEMS Microbiology Reviews, 23, 153-177, (1999)].

However, the amount of heteropolysaccharides produced by lactic acid bacteria is generally low (of the order of 10 to 200 mg per liter of fermented product). To improve the texture, manufacturers of fermented products add other texturing agents, such as stabilizers (modified starches, carrageenan, guar, pectin, gelatin, etc.). However, these additions are not always authorized (for example in natural yogurt), and generally affect the taste and aroma of the product. Optimized production of exocellular heteropolysaccharides (EPS) in the product is therefore preferable.

Given the importance of EPS in the agrofoods industries, mentioned above, many studies have related to methods for increasing the production thereof by optimizing the biotechnological processes by acting on the temperature, the pH and the composition of the medium. These approaches are, however, sometimes difficult to apply in the context of certain agrofoods processes, such as the production of fermented dairy products for which the medium and the fermentation conditions are specific to each type of product. These production constraints therefore limit the use of conventional methods for optimizing the processes in order to improve EPS production. An alternative to these methods would be to use strains suitable for these processes, i.e. strains capable of producing EPS in greater quantity, and/or in which the EPS production may be controlled under the conditions for producing fermented products.

One of the main limitations of EPS production by lactic acid bacteria may come from competition between the biosynthesis of these EPS and other metabolic pathways for the use of available sugars. In fact, although homopolysaccharides are mainly produced by specific extracellular enzymes from substrates present in the medium, the synthesis of heteropolysaccharides takes place at least in part inside the cell. In particular, the formation of heteropolysaccharide precursors (nucleotide sugars), consisting of sugars activated by reaction with triphosphate nucleotides, might involve intracytoplasmic enzymes which also contribute to other metabolic pathways, and in particular to glycolysis. Now, due to the fermentative metabolism of lactic acid bacteria, the glycolysis reactions are more active than those relating to EPS synthesis.

The inventors set themselves the aim of obtaining lactic acid bacteria mutants in which it is possible to control and in particular increase the capacity to use sugars available in the medium, and in particular galactose, to produce EPS.

With this aim, they have investigated the genes involved in the synthesis of nucleotide sugars, the precursors of EPS, and/or the genes involved at the crossroads between the pathways of glycolysis and of EPS biosynthesis. Among the latter, they were more particularly interested in the genes for phosphoglucomutase (PGM), which is involved in the transformation of metabolic derivatives of galactose into glycolysis intermediates, and for glucose-1-phosphate uridyl-transferase, which catalyzes the formation of nucleotide sugars, the precursors of EPS.

DE VUYST and DEGEEST (abovementioned publication) put forward the hypothesis that phosphoglucomutase might play an important linking role between glycolysis and EPS biosynthesis, and that diverting part of the carbon flow to this enzyme might make it possible to increase EPS production. However, they also underline that it remains to be seen whether this can effectively be done.

It has recently been reported [HARDY et al., J Bacteriol., 1854-1863, (2000)] that inactivation in *Streptococcus pneumoniae* of a gene [GENBANK AF165218] encoding a phosphoglucomutase leads to a dramatic decrease in the production of EPS forming the bacterial capsule, and is also highly damaging to cell viability, although this bacterium possesses another pgm gene.

The existence of an α-PGM and a β-PGM has been reported in *L. lactis*; however, only the gene corresponding to β-PGM has been isolated [QIAN et al., Microbiology, 143, 855-865, (1997)]. No gene capable of encoding an α-PGM of a lactic acid bacterium has been genetically characterized to date.

The inventors have now succeeded in cloning and characterizing a pgm gene encoding an α-PGM of *Streptococcus thermophilus*.

This gene is represented in the attached sequence listing under the number SEQ ID NO: 1, and the corresponding polypeptide is represented under the number SEQ ID NO: 2.

A subject of the present invention is a nucleic acid sequence encoding an α-PGM the amino acid sequence of which exhibits at least 70% identity or at least 85% similarity, preferably 80% identity or at least 90% similarity, advantageously at least 90% identity or at least 95% similarity, and most preferably at least 95% identity or at least 99% similarity, with the α-PGM represented by the sequence SEQ ID NO: 2, and also any fragment of more than 20 bp of said sequence.

The percentage identity of a sequence with a reference sequence is defined herein as the percentage of residues of this sequence which are identical to those of the reference sequence when the 2 sequences are aligned so that the positions of the residues correspond to a maximum. A polypeptide the amino acid sequence of which exhibits at least X % identity with a reference sequence can thus comprise up to 100-X modifications per 100 amino acids of the reference sequence. These modifications include the deletion, substitution or insertion of amino acid residues, which may or may not be consecutive.

The percentage similarity of a sequence with a reference sequence is defined herein as the percentage of residues of this sequence which are identical with those of the reference sequence, or which differ therefrom only by one conservative substitution, when the 2 sequences are aligned so that the positions of the residues correspond to a maximum. The term "conservative substitution" is intended to mean the substitution of an amino acid residue with another residue having similar physicochemical characteristics (size, charge or polarity) which do not change the functional properties of the protein. A polypeptide the amino acid sequence of which exhibits at least X % similarity with a reference sequence can thus comprise up to 100-X nonconservative modifications per 100 amino acids of the reference sequence. These modifications include the deletion, nonconservative substitution, or insertion of amino acid residues, which may or may not be consecutive.

The polypeptides thus exhibiting the greatest percentage identities or similarities with the sequence SEQ ID NO: 2, identified by searching on the "GENBANK nr" database using the BLASTp program [ALTSCHUL et al., Nucleic Acids Res., 25, 3389-3402, (1997)], with the default parameters, are as follows:

the ybbT protein of *Bacillus subtilis:* 57% identity and 69% similarity;

the femD protein of *Staphylococcus aureus:* 53% identity and 69% similarity;

the hypothetical phosphoglucomutase of *Streptomyces coelicolor:* 42% identity and 55% similarity;

the mrsA homologue of *Pseudomonas syringae:* 41% identity and 54% similarity;

the mrsA homologue of *Mycobacterium leprae:* 41% identity and 54% similarity.

No significant homology with the pgm gene of *L. lactis* described by QIAN et al. (publication cited above) was observed. The percentage identity with the pgm gene of *S. pneumoniae* described by HARDY et al. (publication cited above) is less than 31%.

The inventors have performed site-directed mutagenesis of the pgm gene of *S. thermophilus*, and have noted that, surprisingly, total or partial inactivation of this gene leads to an increase in EPS production.

A subject of the present invention is also a lactic acid bacteria mutant overproducing EPS, in which the pgm gene of alpha-phosphoglucomutase is totally or partially inactivated.

Said lactic acid bacterium will preferably be a mesophilic or thermophilic bacterium, chosen from *streptococci* and *lactobacilli*. By way of example, it may be *Lactococcus lactis, Streptococcus thermophilus, Leuconostoc mesenteroide, Lactobacillus casei, Lactobacillus delbrueckii, Lactobacillus sake*, etc.

Inactivation of the pgm gene may be obtained by making one or more mutations in the sequence encoding α-PGM, and/or in sequences controlling its expression.

Use may in particular be made of site-directed mutagenesis techniques, which are in themselves known to those skilled in the art and which make it possible to introduce a defined mutation into a gene, at the desired position.

It is thus possible, for example, to inactivate the pgm gene by introducing into the coding sequence, or the regulatory sequences, an exogenous sequence, for example a transposon.

Advantageously, it is also possible to replace the wild-type sequence of the pgm, by homologous recombination, with the mutated sequence. In this case, one or more modifications by insertion, deletion or substitution of one or more nucleotides, which may or may not be consecutive, are made in a sequence identical to that of the region of the gene intended to be mutated.

According to a preferred embodiment of the present invention, the mutated sequence is inserted into a vector which allows integration by recombination (simple crossing-over) between the bacterial DNA fragment cloned into the vector and the homologous region of the bacterial genome. Excision of the vector sequences can then occur following a second recombination event (double crossing-over), which results in substitution of the wild-type chromosomal form by the modified form.

Vectors which allow the integration of an exogenous sequence into the chromosome of a lactic acid bacterium are known in themselves, and are available for most species of lactic acid bacteria; they may, for example, be nonreplicating vectors, unstable replicative vectors or vectors which replicate conditionally, vectors carrying insertion sequences, etc.

In certain cases, it is also possible to transform the bacterium directly with the DNA carrying the mutated sequence intended to be inserted.

Mutants of the pgm gene in accordance with the invention can also be obtained by random mutagenesis (for example by chemical mutagenesis or radiation); they may also be natural mutants selected from cultures of lactic acid bacteria by screening on the basis of their phenotypic properties.

In fact, the mutants in which the α-PGM is partially or totally inactive have normal growth on lactose, and very slow growth on glucose or galactose alone. Such mutants, whether they are natural mutants or are derived from mutagenesis, can therefore be selected directly on the basis of this property.

The presence of mutations in the pgm gene, and the nature of these mutations, can be easily verified with conventional molecular biology techniques, using nucleic acid primers or probes or strains derived from the sequence SEQ ID NO: 1.

If desired, it is also possible to increase or decrease EPS production at will, as a function, for example, of the culturing conditions, by placing the pgm gene under the transcriptional control of an inducible promoter.

The inventors have also cloned and characterized the galU gene which encodes *S. thermophilus* glucose-1-phosphate uridyltransferase. This gene is represented in the attached sequence listing under the number SEQ ID NO: 3. The GalU protein encoded by this gene is represented under the number SEQ ID NO: 4.

A subject of the present invention is also a nucleic acid sequence encoding a glucose-1-phosphate uridyltransferase the amino acid sequence of which exhibits at least 90% identity or at least 95% similarity, and advantageously at least 95% identity or at least 99% similarity, with the glucose-1-phosphate uridyltransferase represented by the sequence SEQ ID NO: 4.

The polypeptides thus exhibiting the greatest percentage identities or similarities with the sequence SEQ ID NO: 4, identified by searching on the "GENBANK nr" database using the BLASTp program [ALTSCHUL et al., Nucleic Acids Res., 25, 3389-3402, (1997)], are as follows:

the glucose-1-phosphate uridyltransferase of *Streptococcus mutans*: 87% identity and 93% similarity;

the GalU protein of *Streptococcus pneumoniae*: 87% identity and 93% similarity;

the UDP-glucose pyrophosphorylase of *Streptococcus pyogenes*: 84% identity and 90% similarity;

the Cap3C protein of *Streptococcus pneumoniae*: 76% identity and 88% similarity;

the UDP-glucose pyrophosphorylase of *Bacillus subtilis*: 55% identity and 74% similarity.

Overexpression of the galU gene makes it possible to increase EPS synthesis by increasing the amount of precursors thereof.

A subject of the present invention is therefore also a lactic acid bacterium mutant overproducing EPS, in which the galU gene is overexpressed. Such a mutant may in particular be obtained by introducing one or more copies of this gene into a lactic acid bacterium, and/or replacing its promoter with a strong promoter. Preferably, said mutant is obtained from a lactic acid bacterium also having a partially or totally inactive α-PGM.

Mutant strains in accordance with the invention may in particular be obtained from *S. thermophilus*, and in particular from *S. thermophilus* strains selected for their ability to grow on galactose. In fact, in this bacterium, another factor which is limiting for EPS synthesis may come from the fact that a large number of strains do not effectively use galactose, whether for growth or EPS synthesis.

The inventors have noted that gal+ strains of *S. thermophilus*, selected for their ability to grow on galactose, can synthesize a larger amount of EPS. Using these clones capable of using galactose for their growth, it is possible to carry out a second selection of the strains producing colonies which appear to be larger in volume, which reflects greater synthesis of EPS.

The use of these gal+ strains of *S. thermophilus*, as starting material for the production of mutants in accordance with the invention, therefore further improves the ability thereof to produce EPS.

Lactic acid bacterial strains in accordance with the invention can advantageously be used for producing fermented products, in particular food products, in which it is desired to control, and in particular increase, the EPS content, and also for producing EPS.

The present invention will be clearly understood by virtue of the further description which follows, which refers to examples of obtaining and using lactic acid bacterial strains in accordance with the invention.

EXAMPLE 1

Selecting *S. Thermophilus* Strains Using Galactose more Effectively for EPS Synthesis A) Strains capable of effectively using galactose were selected using cultures of industrial leavens of *S. thermophilus* from the RHODIA and DANONE collections: RD488 (JIM7446) (RHODIA collection) and ext 1.5 (JIM7459) (DANONE collection).

For this, a 12-hour culture in M17 medium [TERZAGHI and SANDINE, Appl. Microbiol., 29, 807-813, (1975)] containing 1% of lactose is deposited onto M17 agar plates containing 1% of galactose, and is incubated at 42° C. for 2 days. The colonies thus obtained are streaked onto an M17 agar plate containing 1% of galactose, and are incubated at 42° C. overnight. The colonies thus growing on M17 galactose are recovered and grown in liquid M17 containing 1% galactose at 42° C. for 6 hours before being placed in a collection. Other media, such as the chemically defined medium described by SISSLER et al. [Proc. Natl. Acad. Sci. USA, 96, No. 16, 8985-8990, (1999)], in which the sugar source can be controlled, can also be used for this selection.

In order to verify that the strains obtained are indeed capable of more effectively using galactose, the growth of these strains and of the parents thereof are compared.

The growths are carried out as follows: overnight precultures in 10 ml of BELLIKER medium (DIFCO Laboratories) to which 10 g of beef extract/l (DFICO) are added, and containing 1% of galactose, are diluted 100-fold and grown in 2 ml of M17 medium containing 2% of sugar (sucrose, lactose, glucose or galactose) for 4 hours at 42° C. They are then inoculated at 2% into 200 µl of M17 medium containing 1% of sugar. The growth of the strains is then followed using the BIOSCREEN system (LABSYSTEMS).

Figure 1:
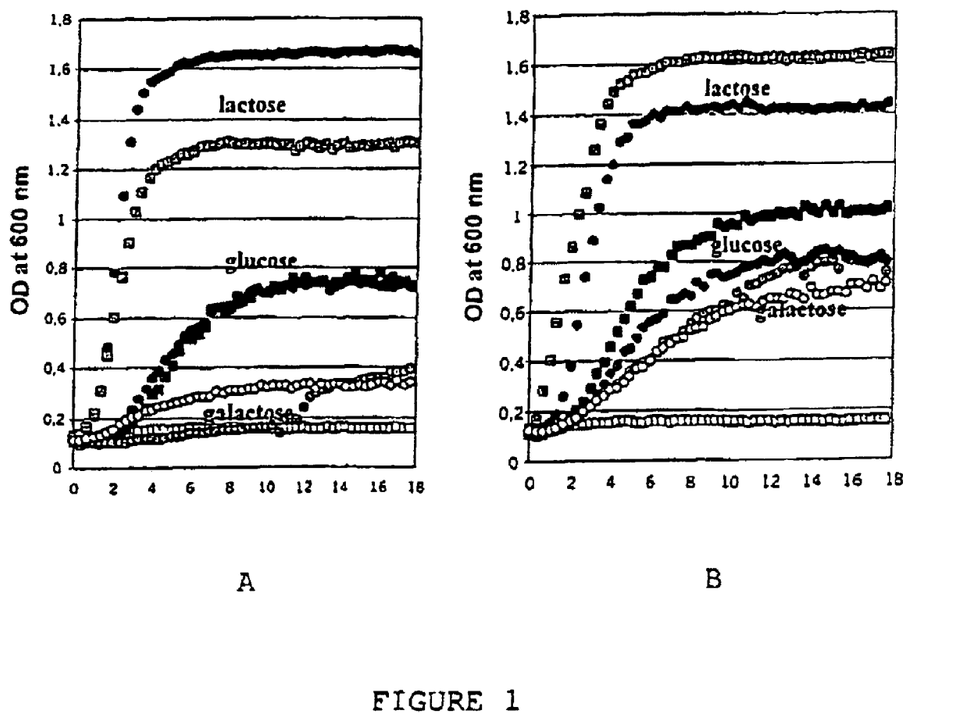

FIG. 1 represents the growth, on various sugars, of the industrial strain JIM7459 (1A) and of a gal+ mutant selected from this strain (1B).

B) It is possible to carry out a further selection from clones already capable of using galactose for growth. Clones producing colonies which appear to have a greater volume are then sought on the plates. These strains use galactose even more effectively.

Figure 2:
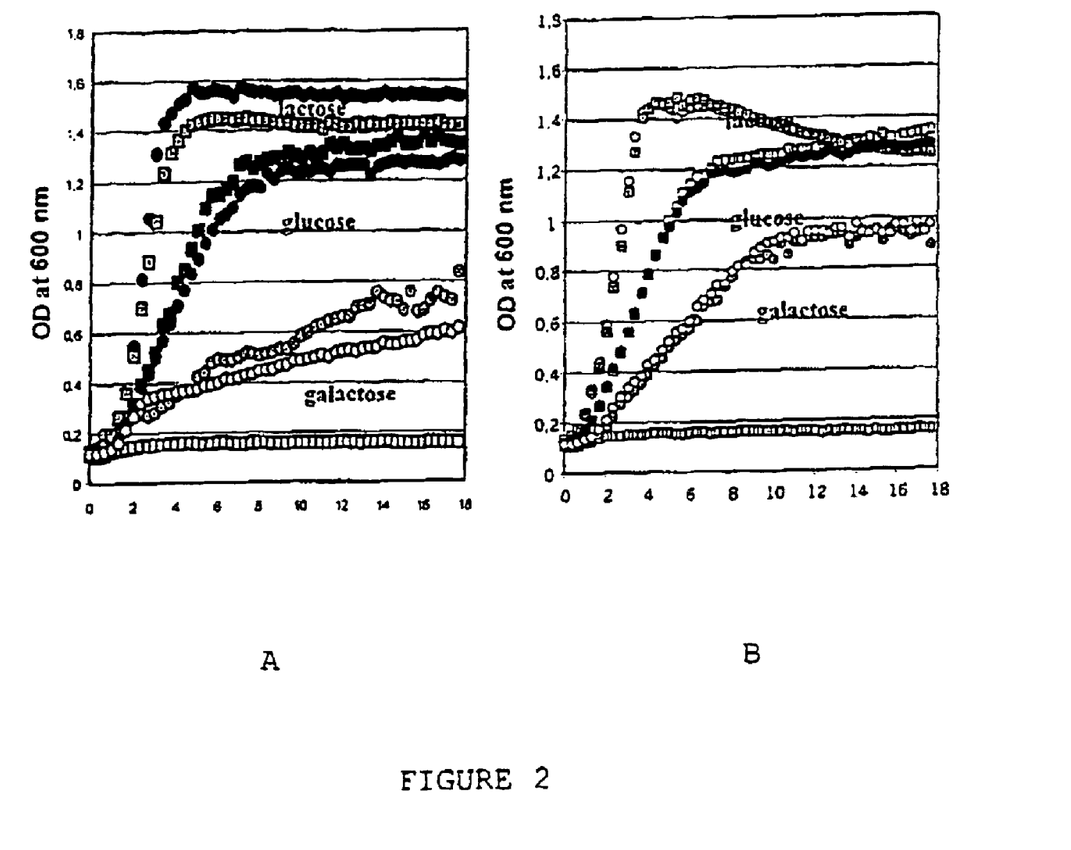

FIG. 2 represents the growth, on various sugars, of a gal+ mutant (2A) selected as described in A above, from a culture of an industrial strain (JIM7446, DANONE collection), and of a gal++ mutant (2B) selected from a culture of this gal+ mutant on the basis of colony size.

After growth of these various strains in chemically defined medium, or in M17 medium, the bacterial pellet of the gal+ mutants is more filamentous than that of the wild-type strains, which may reflect a difference in EPS production between the mutants obtained and their parental strain. The EPS production of these strains was determined from a culture in 80 ml of chemically defined medium [SISSLER et al., Proc. Natl. Acad. Sci. USA, 96, No. 16, 8985-8990, (1999)].

After growth, the cultures are centrifuged at 16 000 g for 10 min at 4° C. The cell pellet is removed and the supernatant is precipitated (2 volumes of 100% ethanol per volume of supernatant) for 24 hours at 4° C. After precipitation, a centrifugation is performed at 16 000 g for 15 minutes at 4° C. The supernatant is removed and the pellet is resuspended in 60 ml of water. Dialysis is performed against water for 4 days, exchanging the water 3 to 4 times per day. The EPS are assayed using the phenol/sulfuric acid method [DUBOIS et al., Analytical Chemistry, 28, 350-356, (1956)].

The results obtained in the case of the 7446 Gal+ strain, and of a mutant of this strain capable of using galactose more effectively, are shown in table I below.

TABLE I

| STRAINS | EPS (mg/l) |
| --- | --- |
| 7446 Gal+ | 4 |
| 7446 Gal++ | 8 |

After growth in the presence of galactose, the strains using galactose more effectively produce increased amounts of EPS.

EXAMPLE 2

Cloning the PGM Gene of *Streptococcus Thermophilus* and Constructing Mutants in which this Gene is Inactive Cloning the Gene:

The pgm gene of *Streptococcus thermophilus* can be obtained by reverse PCR (OCHMAN et al., Biotechnology (NY), 8, No. 8, 759-760, (1990)] from the chromosomal DNA of *S. thermophilus*. The chromosomal DNA of *S. thermophilus* is digested with restriction enzymes (BamHi, EcoRI, HindIII, NcoI, PsI, XhI) and the cleavage products are then circularized then amplified by PCR using the primers complementary to the opposite strand: OST15, OST16, OSY23 to OST26 (table II).

TABLE II

| Primer | Sequence |
| --- | --- |
| OST15 | ACATAACCACCAAAACGACCTAA |
| OST16 | GGAAGCTGAGATGGCTGGTA |
| OST23 | TCTTCAAGAACTGCACGGTCA |
| OST24 | CAAAATTCTTCGTCTTTACCG |
| OST25 | GCTAGCCTTATCGCCAGTCAA |
| OST26 | TTGAGTAAATCAGTTCCAGTT |

The bands obtained are extracted from the gel and sequenced. The sequence of the cloned fragment, comprising the pgm gene and its flanking regions, is represented in the attached sequence listing under the number SEQ ID NO: 1.

The length of the open reading frame of the pgm gene of *Streptococcus thermophilus* is 1350 bp.

Constructing Mutants of the pgm Gene

Figure 3:
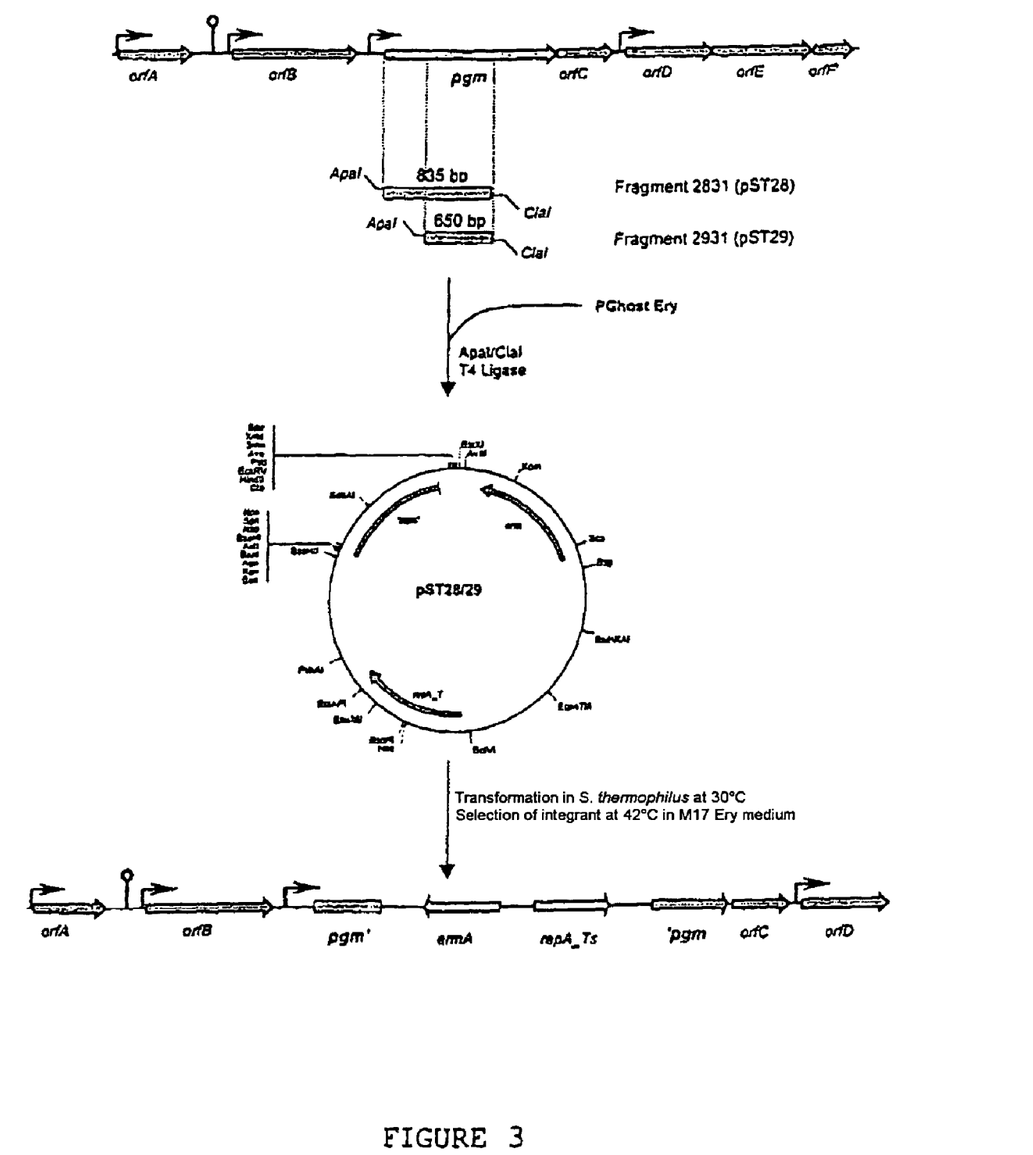

In order to decrease the activity of the pgm gene, the inventors adopted a strategy of inactivation by insertion of a vector into the gene by homologous recombination. The general strategy of inactivation is represented in FIG. 3. Initially, thermosensitive replication plasmids containing fragments internal to the pgm gene were constructed using the thermosensitive replication vector pG+host [BISWAS et al., J. Bacteriol., 175, 11, 3628-3635, (1993); PCT application WO/181164]. Two PCR fragments produced with the oligonucleotides OST29+OST31 and OST28+OST31, and representing, respectively, 650 and 835 bp of the pgm gene, were cloned into pG+host, generating the plasmids pST28 and pST29.

TABLE III

| Primer | Sequence |
| --- | --- |
| OST28 | TAAGGGCCCTAAATATTTTGGAACAGA |
| OST29 | CCGGGGCCCACTTCTCTCAGTAGGTAT |
| OST31 | AATATCGATATTTTCATCAACGGCAAT |

The 650 bp fragment carried by pST28 is central to the gene, it is therefore expected that the insertion thereof should produce total inactivation of the gene. The 835 bp fragment carried by pST29 contains the portion located in the 5' position of the gene with the translation initiation codon, but without its ribosome binding site. It is expected that the insertion of pST29 into the chromosome will cause a very large decrease in translation of pgm, allowing only a very low base expression.

The plasmids pG+host, pST28 and pST29 were introduced by transformation into the *S. thermophilus* strains JIM7446 and JIM7459 at 30° C., and then integrated by simple crossing-over, as shown diagrammatically in FIG. 3. The integration by simple crossing-over was carried out according to the protocol described by BISWAS et al. [publication cited above, (1993)] with the following modification:

The *Streptococcus thermophilus* strains containing the plasmid pG+host or its derivatives are grown overnight at 30° C. in the presence of erythromycin, and then diluted 50-fold in the same medium. They are then transferred to 42° C. for 6 hours. The samples are then diluted and plated out, firstly, at 42° C. on M17 plates containing erythromycin in order to detect the integration events and, secondly, at 30° C. on M17 plates without antibiotic in order to detect the total number of viable cells. The frequency of integration per cell is calculated from the ratio of these counts. The frequencies of integration of these plasmids are, respectively, $3.5 \times 10^{-3}$, $3 \times 10^{-3}$ and $10^{-2}$ for pG+host, pST28 and pST29. Clones derived from each of these integrations were isolated to give the strains STJ3, STJ1 and STJ2, respectively.

The STJ1 (pST28), STJ2 (pST29) and STJ3 (pG+host) strains were grown on plates of chemically defined medium containing glucose and galactose or on plates of the same media containing either glucose alone or galactose alone. The results obtained are given in table IV.

TABLE 4

| Plasmid strains | Growth on CDM Glu Gal Ery | Growth on CDM Glu Ery | Growth on CDM Gal Ery |
| --- | --- | --- | --- |
| STJ1 pST28 | Normal | No growth | No growth |
| STJ2 pST29 | Normal | No growth | No growth |
| STJ3 pG + host | Normal | Normal | Normal |

The STJ1 and STJ2 clones do not therefore grow on glucose or galactose alone, but grow normally in lactose or on a glucose and galactose mixture. This shows that glucose and galactose metabolism has indeed been uncoupled in this strain and that the gene whose activity has been affected is indeed pgm.

These results show that the inactivated gene clearly encodes an enzyme which connects the EPS pathway and glycolysis. It therefore probably encodes α-PGM, the sequence of which had not yet been characterized experimentally in lactic acid bacteria.

Assaying the EPS Produced by the *Streptococcus thermophilus* Strain STJ2 Carrying a Mutation in the pgm Gene The EPS are assayed as described in example 1 above.

The EPS production in the strain affected in terms of expression of the pgm gene is 20 mg/l. This production, compared to the 8 mg/l obtained for the parental strain 7446 Gal++, therefore corresponds to a two and a half-fold increase.

EXAMPLE 3

EPS Production by pgm Gene Mutants Derived From Industrial Strains

The plasmid pST29 described in example 2 above was used to transform the industrial strains (DANONE collection) Ext 1.1 (JIM7455) and Ext 1.10 (JIM7464). These strains produce EPS with different compositions (1-glu:2-gal: 1-galNac for Ext 1.1 and 3-gal: 1-rha for Ext 1.10), and which are also different from that produced by the JIM7446 strain (3-glu:4-gal).

After electroporation, the cells are plated out at 30° C. for 12 h and the plates are then placed at 42° C. in order to force integration of the plasmid pST29 into the pgm gene by homologous recombination between the pgm sequences present on the plasmid and those present on the chromosome. Colonies of mutated bacteria capable of growing at 42° C. in the presence of erythromycin were obtained. These bacteria are also capable of growing on CDM (chemically defined medium), in the presence of glucose and galactose, but not in the presence of glucose alone or galactose alone.

The transformed or untransformed strains were cultured in 10 ml of CDM containing 2% lactose, 1.5% casitone and 10 mM urea, in the presence of erythromycin (5 µg/ml) for the strains transformed with the plasmid pST29. The EPS produced by the various strains were assayed after 67 h 30 min of culturing at 42° C. The results obtained are given in table V below.

TABLE V

| Strain | $OD_{600}$ | pH | mg EPS/l | mg EPS/l/OD |
|---|---|---|---|---|
| 7455 (Ext 1.1) | 1.566 | 4.6 | 12.5 | 8 |
| 7455::pST29 | 0.98 | 4.6 | 14.68 | 16 |
| 7464 (Ext 1.10) | 1.29 | 4.24 | 23.6 | 18.29 |
| 7464::pST29 | 0.99 | 4.2 | 44 | 44 |

It is noted that the strains in which the pgm gene is inactivated in accordance with the invention produce, at equal biomass, 2 to 2.5 times more EPS than the strains of origin.

EXAMPLE 4

Constructing a Mutant of the pgm Gene by Double Crossing-Over

A vector named pSTJ6, containing a pgm gene inactivated by internal mutation, was constructed by reverse PCR amplification using the plasmid pST29 as matrix and the following primers, derived from the sequence of the pgm gene with point mutations, inducing in particular the creation of an NsiI site:

GAC<u>A</u>*TGCA*<u>T</u>CGCTTGTCGATTA<u>G</u>CCAGAAGGTC

GCG<u>A</u>*TGCA*<u>T</u>GTC<u>A</u>TT<u>A</u>AGCTGATGGGCGTCGAAG

The mutations introduced into the primers are underlined: the NsiI site created is indicated in italics.

The PCR product is cleaved with NsiI and religated on itself to give the vector pSTJ6.

This vector is introduced by transformation into the *S. thermophilus* strain JIM7446.

The colonies are plated out at 30° C. for 12 h, and then grown at 42° C. for 24 h in order to force the integration of the vector into the chromosome via a first crossing-over by recombination between the pgm sequences present on the plasmid and those present on the chromosome. The colonies thus obtained, erythromycin resistant and capable of growing at 42° C., are then grown at 30° C. in order to promote excision of the pG+host plasmid sequences via a second crossing-over by recombination between the pgm sequences present on either side of the pG+host sequences. pG+host is then removed from the cell by a step of growth at 42° C. in the absence of selection with erythromycin. The strain thus obtained no longer contains any sequences of the vector pG+host and, in particular, it does not contain a gene for resistance to antibiotics.

It differs from the *S. thermophilus* strain of origin, JIM7446, only by the presence of the mutations in a portion of the pgm gene. The initial sequence and the mutated sequence of this portion of the pgm gene are shown below; the mutations are underlined.

Initial sequence:

GCTGAAGGACTTGGAACGCTTGTCGATTATCCA

Mutated sequence:

GCT<u>TAAT</u>GAC<u>A</u>TG<u>C</u>ATCGCTTGTCGATTA<u>G</u>CCA

The mutated strain has the phenotype characteristic of the pgm mutants, described in examples 2 and 3 above. It is capable of growing on CDM in the presence of glucose and galactose but not in the presence of glucose alone or galactose alone. The increase in EPS production by this strain, relative to the parental strain, is comparable to that observed in the case of the strains transformed with pST29, described in examples 2 and 3.

EXAMPLE 5

Constructing Mutants Overproducing galU

Cloning the galU gene encoding glucose-1-phosphate uridyltransferase

The entire galU gene can be obtained by reverse PCR [OCHMAN et al. (1990), publication cited above] from the chromosomal DNA of *S. thermophilus*, using primers complementary to the opposite strand (OST13, OST14, OST21 and OST22) (table VI).

TABLE VI

| Primer | Sequence |
|---|---|
| OST13 | CCAAGATATCTTCAATACCAGAC |
| OST14 | GAAAACACAACGCGTCTTTGC |
| OST21 | GCACCAGCACCGACTGCGATA |
| OST22 | ACTGGGTAGTTAAACGGTAAT |

The bands obtained are extracted from the gel and sequenced.

The sequence of the cloned fragment, comprising the galU gene, is represented in the attached sequence listing under the number SEQ ID NO: 3.

The size of the galU gene is 914 bp.

Overexpression of GalU

The galU gene (with its terminator and its ribosome binding site) was amplified with the oligonucleotides OST44 and OST45 (table VI) and cloned downstream of the p45 promoter [SIBAKOV et al., Appl. Environ. Microbiol., 57, 341-348, (1991)] of *L. lactis* in the ApaI site.

TABLE VI

| Primer | Sequence |
| --- | --- |
| OST44 | AATGGGCCCAAAAATAAAAAATCTAAGGAG |
| OST45 | AAGCTGCAGACTTATCTTTAAATTAAATGA |

Figure 4:
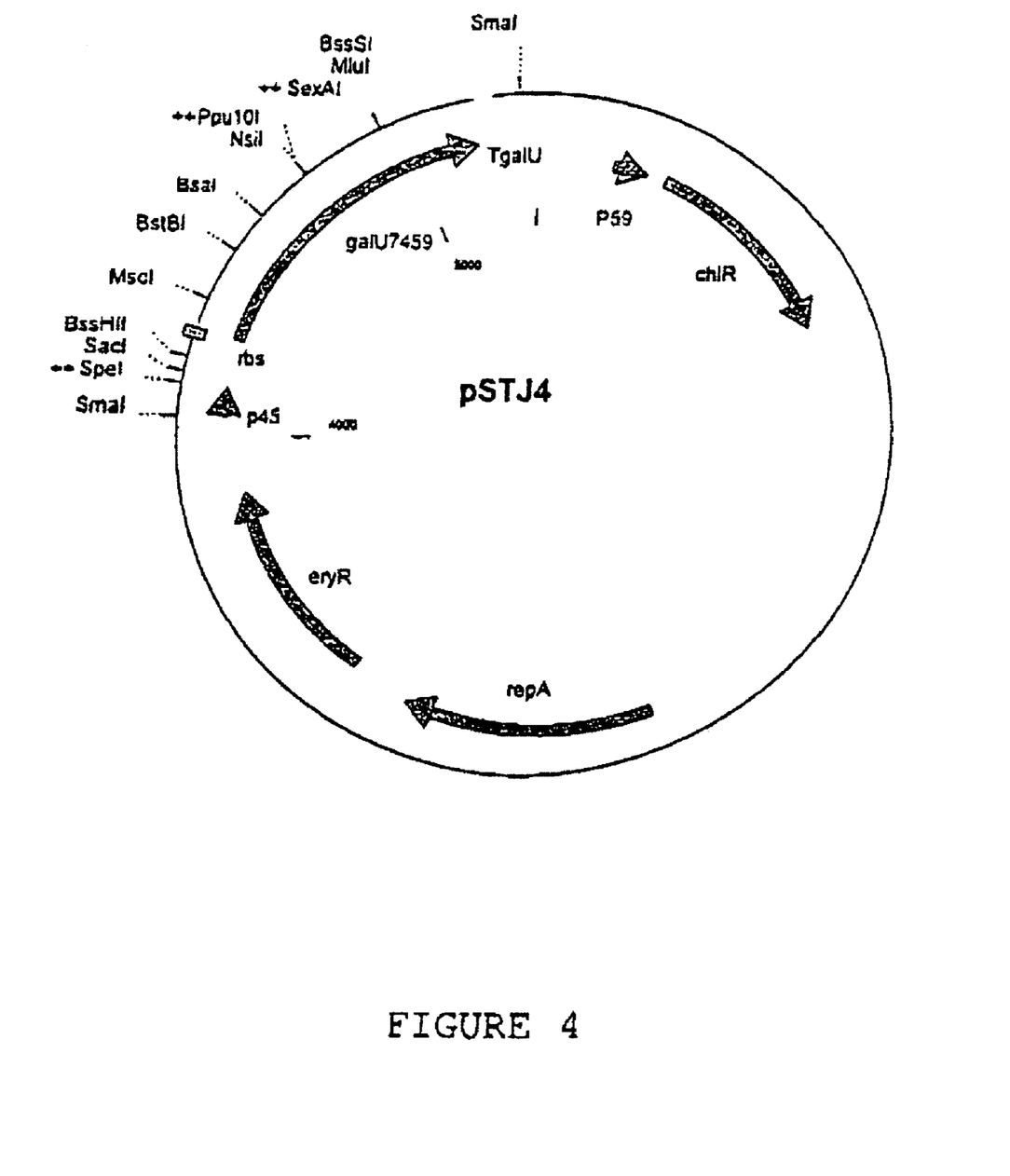

A SmaI fragment of the resulting plasmid, carrying P45 followed by galU, was purified and inserted into the SmaI site of the vector pGKV259 which replicates in *S. thermophilus*. The plasmid pGKV259 [VAN DER VOSSEN et al., Appl. Environ. Microbiol., 53, 2452-2457, (1987)] expressing the galU gene under the control of the p45 promoter is called pSTJ4 (FIG. 4). This plasmid is introduced by transformation into the *S. thermophilus* strain JIM7446 or JIM7459 or into the strain containing a mutation in the pgm gene (STJ2).

The invention claimed is:

1. A lactic acid bacterium having a mutation in the gene encoding a protein having an amino acid sequence with at least 80% identity to SEQ ID NO: 2, wherein said mutation totally or partially inactivates said gene and enhances the production of exopolysaccharides by said bacterium.

2. The mutant as claimed in claim 1, wherein a gene encoding a protein having an amino acid sequence with at least 95% identity to SEQ ID NO: 4 is overexpressed, and wherein said overexpression further enhances the production of exopolysaccharides by said bacterium.

3. The mutant as claimed in claim 1, characterized in that said lactic acid bacterium is *Streptococcus thermophilus*.

4. The mutant as claimed in claim 1, characterized in that it is obtained from a *Streptococcus thermophilus* strain capable of growing on galactose.

5. The mutant as claimed in claim 1, wherein said gene encodes a protein having an amino acid sequence with at least 90% to SEQ ID NO: 2.

* * * * *

UNITED STATES PATENT AND TRADEMARK OFFICE
CERTIFICATE OF CORRECTION

| | | |
|---|---|---|
| PATENT NO. | : 7,241,610 B2 | Page 1 of 1 |
| APPLICATION NO. | : 10/257737 | |
| DATED | : July 10, 2007 | |
| INVENTOR(S) | : Anba et al. | |

It is certified that error appears in the above-identified patent and that said Letters Patent is hereby corrected as shown below:

Title page, Item (73) Assignee: Please add,

--Compagnie Gervais Danone, Levallois-Perret, France, and Rhodia Chimie, Boulogne Billancourt, France--

Signed and Sealed this

Second Day of September, 2008

JON W. DUDAS
*Director of the United States Patent and Trademark Office*

UNITED STATES PATENT AND TRADEMARK OFFICE
CERTIFICATE OF CORRECTION

PATENT NO. : 7,241,610 B2 Page 1 of 1
APPLICATION NO. : 10/257737
DATED : July 10, 2007
INVENTOR(S) : Anba et al.

It is certified that error appears in the above-identified patent and that said Letters Patent is hereby corrected as shown below:

Title page, item (73) Assignee: Please add,

--Compagnie Gervais Danone, Levallois-Perret, France, and Rhodia Chimie, Boulogne Billancourt, France--

Signed and Sealed this

Seventeenth Day of February, 2009

JOHN DOLL
*Acting Director of the United States Patent and Trademark Office*

SEQUENCE LISTING

```
<160> NUMBER OF SEQ ID NOS: 4

<210> SEQ ID NO 1
<211> LENGTH: 5853
<212> TYPE: DNA
<213> ORGANISM: Streptococcus thermophilus
<220> FEATURE:
<221> NAME/KEY: CDS
<222> LOCATION: (2169)..(3092)

<400> SEQUENCE: 1
aagataccca tagtagtttt tatagtcagg gtttaattgt tatcataaaa agtagtgatt      60
gtagcctcaa aatagtttga attcatggta taatagaaac tgttaaaaaa ttaaaagaaa     120
gtgtgatgag tatgggatta ctttcgtcca ttgacgttga ttttttggcgg tcactttttg     180 atagtccgct gagggttctt gtcaatagtt tggacatatt gattgttgct tttttaattt     240
atcggtttat tagggctctg agaggaacaa aaatcatgac cctagtccaa ggggtagtct     300
tatttatttt tgtaaagatt atctctgatt ttattggatt cacgacgatt tcttatttga     360
tgaatcaagt catcaattat ggtgctattg cagcagtcgt tattttttgcg ccagaacttc     420 gttcggcact tgagacattt ggacggacac ctcagcattt tttgcaaaat aaagaggtca     480
gttcagatga gaaattggtt caggcttttg tcaaggccgt caagtatatg agcccgcgta     540
agattggagc cttggtttct attgaacaaa ctcagacttt acaagaacag attgcgacag     600
ggattccgct aagatgcagt ggtgactggg gaacttctaa taaatatctt cataccaaat     660
acgccgcttc atgatggtgc agtaattata agagataata aggttacaac agcttgttct     720
tatctgccat tatcagagtc taataagatt tccaaagaat ttgggacaag acacagggct     780
gctattggtc tttcggaaca aacagatgca ctaacctttg ttgtctctga ggaaacgggt     840
gcgatttcca ttgcgtacaa gggcaatttt ttgcacgacc tctcagttca agaatttgaa     900
catgagttaa gtcttatctt gttgaaagag caggaaccac gtcagttatt ctttcaacgt     960
tggattggag gtggtgaaaa atgaagcgtc tagtaagatt tttcacaaat gatcgcttgt    1020
ggcagatggt agttgccctc ttccttgctg tcacactctt tttcacagca tggtcgggga    1080
atacacaaaa taaaaataat agctcaattg catccaaatc tttcacgaaa accgttgagt    1140
cggtacctgt ggatatcaaa tacgatagtg ataagtactt tatcagtggc tattcctatg    1200
```

-continued

```
atgctgaggt ctatctaaca gcgacgacac aattagcctt gacaactgaa acaacaagtg   1260
acacacgtca ttttaagttg gttgcagatt tatcaaattt tggcccaggg acaagtcatg   1320
ttcctattca ggttaagaat ttaccggatg gaatgtctgc ccaagtatca ccatcgacct   1380
tgacagcaac tataggtaaa aaagctagta agacatttga tgtagttgca aatatcacac   1440
cggataagtt ggctaatggc tatgaagtga aaaaggttag cttggatgaa accaaggtag   1500
aggtgacctc aagtgaggat atcatcaatc aaattgatca cgttcaagca gtcttggaag   1560
gcgatgacaa cttgtctgat gattatgatg gtaacttggt tcttcaagca gtttcgtcta   1620
atggaacgat tttagctagt tcaatttccc cagctaaggt tcatgccaag attagtttga   1680
gaaaattgag taaatcagtt ccagttaagc tagagttgac tggcgataag gctagcaatg   1740
tgtctagtat cagttatagt tttgatcgtg gtcatgtgac cattgttggt agtcaagaag   1800
ccatggataa aattgatagc atcacagtcc ctgtagacat tagccaagta actaaagata   1860
catcgaaaac cttagagcta aaagcagaag gtgttacagt gcagccaagt actgtgaagg   1920
ttaacttgaa agtcacgcaa aagtgaggga gttacatttt catcaaattg agatataata   1980
gattgggttg agaggaatag tctcataata atgtaaccaa ttaataatat tttaaaacaa   2040
gggttgaaca tattggtgca atcttataca gctagattat ctagataggt tcactagatt   2100
agattgactc ttgctaatgg catcaaagtt taaggaggat ttagtgcaca ggcactaata   2160 gtaaattt atg gga aag tat ttt gga aca gac ggt gtt cgt gga gaa gca   2210
         Met Gly Lys Tyr Phe Gly Thr Asp Gly Val Arg Gly Glu Ala
           1               5                   10 aac gtt gag ctt acg cct gaa ttg gct ttt aaa tta ggt cgt ttt ggt    2258
Asn Val Glu Leu Thr Pro Glu Leu Ala Phe Lys Leu Gly Arg Phe Gly
 15                  20                  25                  30 ggt tat gtg ctt agt caa cat gaa act ggc cgt cct aaa gtt ttt gtg    2306
Gly Tyr Val Leu Ser Gln His Glu Thr Gly Arg Pro Lys Val Phe Val
                 35                  40                  45 gct cgt gat aca cgt att tct ggt gag atg tta gaa tct gct ttg gta    2354
Ala Arg Asp Thr Arg Ile Ser Gly Glu Met Leu Glu Ser Ala Leu Val
             50                  55                  60 gcg gga ctt ctc tca gta ggt atc gaa gtc tat aaa ctt ggg gta ctt    2402
Ala Gly Leu Leu Ser Val Gly Ile Glu Val Tyr Lys Leu Gly Val Leu
         65                  70                  75 gcg aca cca ggt gta tca tac ttg gta cgt aca gaa aat gct agt gct    2450
Ala Thr Pro Gly Val Ser Tyr Leu Val Arg Thr Glu Asn Ala Ser Ala
     80                  85                  90 ggt gta atg att tca gct agt cac aat cca gca ctt gac aat gga atc    2498
Gly Val Met Ile Ser Ala Ser His Asn Pro Ala Leu Asp Asn Gly Ile
 95                 100                 105                 110 aaa ttc ttt ggt gga gat ggc ttt aaa tta gat gat gca cgt gaa gcg    2546
Lys Phe Phe Gly Gly Asp Gly Phe Lys Leu Asp Asp Ala Arg Glu Ala
                115                 120                 125 gaa att gaa gct ctc cta gat gcc gca gaa gat act ctt cca cgc cca    2594
Glu Ile Glu Ala Leu Leu Asp Ala Ala Glu Asp Thr Leu Pro Arg Pro
            130                 135                 140 tca gct gaa gga ctt gga acg ctt gtc gat tat cca gaa ggt ctt cgt    2642
Ser Ala Glu Gly Leu Gly Thr Leu Val Asp Tyr Pro Glu Gly Leu Arg
        145                 150                 155 aaa tac gaa aaa ttc ttg gtg act act ggt ctt gac ctc ggt ggt atg    2690
Lys Tyr Glu Lys Phe Leu Val Thr Thr Gly Leu Asp Leu Gly Gly Met
    160                 165                 170 aag gtt gcc ttg gat gct gct aac ggt gcg gct gcg gta tct gct cgt    2738
Lys Val Ala Leu Asp Ala Ala Asn Gly Ala Ala Ala Val Ser Ala Arg
175                 180                 185                 190
```

| | |
|---|---|
| aat att ttc ctt gac ttg aat gca gaa atc gct gtt att ggt gat caa<br>Asn Ile Phe Leu Asp Leu Asn Ala Glu Ile Ala Val Ile Gly Asp Gln<br>195 200 205 | 2786 |
| cct gat ggc ctt aat atc aat gct ggt gta ggt tct aca cat cca gag<br>Pro Asp Gly Leu Asn Ile Asn Ala Gly Val Gly Ser Thr His Pro Glu<br>210 215 220 | 2834 |
| caa ttg cag gcc tta gtt aga gaa tct ggt tca gca atc ggt ctt gcc<br>Gln Leu Gln Ala Leu Val Arg Glu Ser Gly Ser Ala Ile Gly Leu Ala<br>225 230 235 | 2882 |
| ttt gat ggt gtc agt gac cgt ctc att gcc gtt gat gaa aat gac gat<br>Phe Asp Gly Val Ser Asp Arg Leu Ile Ala Val Asp Glu Asn Asp Asp<br>240 245 250 | 2930 |
| att gtc gat ggt gac aag gtg atg tat atc att ggt aaa tac ttg tct<br>Ile Val Asp Gly Asp Lys Val Met Tyr Ile Ile Gly Lys Tyr Leu Ser<br>255 260 265 270 | 2978 |
| caa aaa ggt gag tta gct aaa aac acc att gtt aca aca gtt atg tca<br>Gln Lys Gly Glu Leu Ala Lys Asn Thr Ile Val Thr Thr Val Met Ser<br>275 280 285 | 3026 |
| aat ctt ggt ttc cac aag gct ctc gcc cgt gaa ggt att aac aag act<br>Asn Leu Gly Phe His Lys Ala Leu Ala Arg Glu Gly Ile Asn Lys Thr<br>290 295 300 | 3074 |
| gtg atc tgc tgt tgg tga ccgttacgtt gttgaagata tgcgtatata<br>Val Ile Cys Cys Trp<br>305 | 3122 |
| cggttataat cttggtggcg aacagtctgg tcacgttatt atcatggatt acaataccac | 3182 |
| cggtgatggt caattgacag ctatccaatt gactaaagta atggttgaaa caggtaagag | 3242 |
| cttgtctgaa ttagcagcag aagtaaccat ttaccctcaa aaattagtta atatccgtgt | 3302 |
| ggaaaatagc atgaaagata aagctatgga cgttcctgca attgccgcta tcattgaaaa | 3362 |
| aatggaagct gagatggctg gtaatggacg tatcttggtt cgtccaagtg gtacagagcc | 3422 |
| tctccttcgt gttatggccg aagcaccaac agatgatgaa gtgaactact atgtcgatac | 3482 |
| tattgccgat gttgttcgtg cagaaattgg tttggactaa gtatgctagc taaactcaga | 3542 |
| ggctttatgg ctaccgaagt tttcaaatat ctcttctttg gattttggc aactttggtt | 3602 |
| tacatggtta gtcgtacctt gattttcag ttgaccaaac aagggaccct ctcggctgtc | 3662 |
| ctggccaatg cgattgccat tatctttgcc ttttttacaa atgacatctt tgtctttaat | 3722 |
| caggaaacgg caggtatggc cacgcgcttt gttaagttcg taggagcccg ccttttgacc | 3782 |
| ttggtcttgg atttggcatt agcctatttc ttggtagata cttatccaga gattattggt | 3842 |
| caatttgttg gccatagtca ggcatgggta atggtatcg agagtctatt tgctcaggtc | 3902 |
| cttatcattg tgttgaacta tattatttca aaattcttcg tctttacgga cgaaaaagta | 3962 |
| taaacaaaaa ggaagttgtt aggcaaatgt gttaaaagcg tttcttaccg acctcctttt | 4022 |
| ttgatataat tgaagagact taaaaaatag aaagatgaaa catgtacgta caattatctc | 4082 |
| aacgtctcaa ggacgtagca acctacgttc ctaaaggcgc aaaactcttg gatgtaggaa | 4142 |
| gtgatcatgc ctatcttcca atttatctac ttgaaaaggg cttgattact tcagccattg | 4202 |
| ctggcgaagt ggtaaagggt ccttatgaat cagctctcgc aaatgtctca gcttctggtt | 4262 |
| tcaatgataa aatcgacgtg cgcttggcga atggcttagc tgcctttgag ccttatgatg | 4322 |
| ccgttacaac tatcacgatt tgtggtatgg gggacgtct tattgcggat attcttgatg | 4382 |
| ctggaaagga caaacttaag gacgtagacc gtctgatttt gcaaccaaat aatcgagaag | 4442 |
| atgatctccg tatctggttg atgaaaaatg gttttactat tgttgcagaa gccattatga | 4502 |

```
ctgaaaatgg caaatattac gaaatcatag tggcagaagc tggtcaaatg aacctttcag   4562
agagggagat tcgctttggc cctcatctta tgaaagagca gtctcaggtt ttcaagctca   4622
aatggcaacg tgaaattaat aaattagaga ttgccttggg gtctattccc cttgccaatc   4682
aggatgaccg tgcagttctt gaagaaaaaa ttcaaaccat taaggaggtt ttggaccatg   4742
ttagctagtg atcttatcaa gtcttatgaa agcttttgtc caccggaact ttccatggaa   4802
ggtgatgtgg ttggcttaca aattggcagt ctggataagg agattcagaa ggtcatggtt   4862
actttggatg ttcgtgagaa tacagtagct gaagtcattg aaaaaggtgt ggaccttatc   4922
attgctaagc atgcacctat tttccgtcct gtaaaggatt tggtgtcgtc accgaccgt    4982 gatattttgc ttgacctagt taagcacgac attgctgtct atgtcagtca taccaatatt   5042
gatgtcgttg atgaaggtct taatgattgg ttctgcgagt tacttgacat taaggatacc   5102
acttatttaa cagagactgc tgaaaatcaa ggaatcggtc gagtgggtga tattgtgcca   5162
cagaccattg aagatcttgc tcttaaagtc aagtctgctt ttggtttaga tagtgttcga   5222
ctggttcgtt ataatcatga caatcctctt gttaaccgtg tggctatttg cggtggtagt   5282
ggtcaaggat tttacaagga tgctctgaaa aagggagcac aggtttttat cacgggagat   5342
atttattacc atacgggtca agagatgatt actaacggcc tcttggctat tgaccccggt   5402
caccatatcg aagccctctt tgtctcaaag attgctgaga acttgaggt ctggaaacgt    5462 gagcataatt ggcatgtgac gatacttgaa agtcagtcgt caacaaatcc ttttgatcat   5522
ttgtaggtgg atttgtttat gacttggttt ttacatcaaa atgttgtttt cttagctttt   5582
cttgccggtc tctttacctg aggatgtact attgttggct cagccatagt tttcttcttc   5642
aagaatatta gccgtaaatt gcaagacatc atgatgggct ttgcggctgg tgtcatgatt   5702
gcagcctctt tttggtccgc tactggctcc ttctttggct tatgccagtc aaaatggata   5762
tggtaaattg tcatggtttc ccgcagcagc tggattctta cttggtggtg ttgccccttc   5822
gtttgattga tgctgtcgtc cctcacttgc a                                   5853
```

<210> SEQ ID NO 2
<211> LENGTH: 307
<212> TYPE: PRT
<213> ORGANISM: Streptococcus thermophilus

<400> SEQUENCE: 2

```
Met Gly Lys Tyr Phe Gly Thr Asp Gly Val Arg Gly Glu Ala Asn Val
 1               5                  10                  15

Glu Leu Thr Pro Glu Leu Ala Phe Lys Leu Gly Arg Phe Gly Gly Tyr
            20                  25                  30

Val Leu Ser Gln His Glu Thr Gly Arg Pro Lys Val Phe Val Ala Arg
        35                  40                  45

Asp Thr Arg Ile Ser Gly Glu Met Leu Glu Ser Ala Leu Val Ala Gly
    50                  55                  60

Leu Leu Ser Val Gly Ile Glu Val Tyr Lys Leu Gly Val Leu Ala Thr
65                  70                  75                  80

Pro Gly Val Ser Tyr Leu Val Arg Thr Glu Asn Ala Ser Ala Gly Val
                85                  90                  95

Met Ile Ser Ala Ser His Asn Pro Ala Leu Asp Asn Gly Ile Lys Phe
            100                 105                 110

Phe Gly Asp Gly Phe Lys Leu Asp Asp Ala Arg Glu Ala Glu Ile
            115                 120                 125

Glu Ala Leu Leu Asp Ala Ala Glu Asp Thr Leu Pro Arg Pro Ser Ala
```

```
                130                 135                 140
Glu Gly Leu Gly Thr Leu Val Asp Tyr Pro Glu Gly Leu Arg Lys Tyr
145                 150                 155                 160

Glu Lys Phe Leu Val Thr Thr Gly Leu Asp Leu Gly Gly Met Lys Val
                165                 170                 175

Ala Leu Asp Ala Ala Asn Gly Ala Ala Ala Val Ser Ala Arg Asn Ile
            180                 185                 190

Phe Leu Asp Leu Asn Ala Glu Ile Ala Val Ile Gly Asp Gln Pro Asp
        195                 200                 205

Gly Leu Asn Ile Asn Ala Gly Val Gly Ser Thr His Pro Glu Gln Leu
    210                 215                 220

Gln Ala Leu Val Arg Glu Ser Gly Ser Ala Ile Gly Leu Ala Phe Asp
225                 230                 235                 240

Gly Val Ser Asp Arg Leu Ile Ala Val Asp Glu Asn Asp Asp Ile Val
                245                 250                 255

Asp Gly Asp Lys Val Met Tyr Ile Ile Gly Lys Tyr Leu Ser Gln Lys
            260                 265                 270

Gly Glu Leu Ala Lys Asn Thr Ile Val Thr Thr Val Met Ser Asn Leu
        275                 280                 285

Gly Phe His Lys Ala Leu Ala Arg Glu Gly Ile Asn Lys Thr Val Ile
    290                 295                 300

Cys Cys Trp
305

<210> SEQ ID NO 3
<211> LENGTH: 4151
<212> TYPE: DNA
<213> ORGANISM: Streptococcus thermophilus
<220> FEATURE:
<221> NAME/KEY: CDS
<222> LOCATION: (2091)..(3005)

<400> SEQUENCE: 3
aagcttggaa aaacagatta gatgaacttt acagaaggta ttactgctaa tatgttcgtc        60
aaccttgcta tcttgggcta tatgctcctc aaagaagagt ctgccaagat tttcattgcc      120
ctatcagcta tcttcatgtt tgtcttttg gtgaatgaac acttgattgc aaactttgca      180
tctttcatgt tactcggttt caacggtatc cgtgatgctg tggacaattt cacattagca      240
aatattctac atcagtgggt aatcgttttc ttcggcaact ggattggtag cggtattttc      300
attggtttgg catactcttg gctcaataaa accaaaacaa ctcacatcga ttaggaggct      360
agatgcgtca aaagatattt atcaaacaaa cttgccgagc tcttctactg tattttatat      420
gcctaaccat tgcagttgcg attgatttaa tcttttttaa agtcaaaaac atgtaccaca      480
cacctgcctt ggtggctatc ttttcgggct gggtttattt agggctaatc caaagacca       540 aacaatttgg agctgttacc tgccttggtc tcttcatgtc catcttcttc tttacctctg      600
gtcactttgt cctaaccttc cttccaagtt tgctggctgg ccttggcgct gacttactcg      660
ccaagaaggg caactatgag aactatgaga atgataaagt aaatctactt tcctatatgg      720
tcttttctct gggaaacttg gcacctatag tgaccatgtg gctagctcct aaagcctaca      780
gtgcacaact cttagctaaa ggcaaaacac aagattaggt agaccaagtt atggtcccat      840
tcacagccaa tcatgctcta atcctgattg gcggaactct tatggctgct ctcattggag      900
gccacattgc taaaaattgg ctaaaaaata aatagccagc aatcttccta acagagcgga      960
caagacaaac tcgcttctct tatgctataa tgagaaagaa tatagtcttt ttctgctttg     1020
```

-continued

```
ttagaaagga cataaaggga gaccgaatga tgaaaaaaca aaaaatcgct gtcttgggcc      1080
ctggttcttg gggaacagct ctcgctcagg tactcaacga taacggacac gaggtccgta      1140
tttggggaaa catccctgaa caaattgatg aaatcaacga aaaacatacc aatacccgct      1200
attttaaaga tgtgattttg gatgaaagca ttaaagccta caagagcta tctgaagcct       1260 tagatagtgt taatgctatt ctctttgttg ttccaactaa ggtcactcgc ttagttgcta      1320
agcaagttgc cgaacttta gaccacaaag ttgttgtcat gcatgcttca aaaggtttgg       1380
aaccaggaac acacgaacgc ctctctacaa tccttgaaga ggagattcct tcggaaatgc      1440
gaagtgagat tgtcgttgta tctggcccaa gtcatgctga agaaactatt gttcgtgaca      1500
tcaccctgat tacagcagca tctaaggacc ttgaaacagc aaggtatgtc caaggtattt      1560
ttagtaatag ctatttccgt tctctacacta actctgatgt gattggtgtt gaaacagccg     1620
gtgcccttaa aaacattatc gcagtcggtg ctggtgctct ccatggtatg gctatggag       1680 acaacgctaa ggcagccata attactcgag gactggcaga atcactcgt cttggtgtaa       1740 aactcggagc tgacccttg acttacagcg gtctatctgg cgttggcgac ctcatcgtta       1800
ctggaacttc tatccattca cgtaactggc gtgccggata tgcgcttggt cgtggcgaaa     1860
aactagaaga cattgaacgt aacatgggta tggttatcga aggaatttca accactaagg     1920
ttgcctacga aatcgctcaa gaacttggcg tctacatgcc aattacaaca gcaatctaca    1980
aatctatcta tgagggtgct gatatcaagg aatctattct caatatgatg tccaatgaat    2040
tgcgctctga aatgaatgg gataaaaaat aaaaatcta aggagttctc atg aaa          2096
                                                        Met Lys
                                                         1 aat caa aaa gtt aga aaa gct gtc atc ccc gct gga gga ctt gga aca       2144
Asn Gln Lys Val Arg Lys Ala Val Ile Pro Ala Gly Gly Leu Gly Thr
         5                  10                  15 cgc ttt tta cca gct act aaa gca ttg gcc aaa gaa atg ttt cca atc       2192
Arg Phe Leu Pro Ala Thr Lys Ala Leu Ala Lys Glu Met Phe Pro Ile
 20                  25                  30 gtt gac aaa cca acc atc caa ttt atc gtt gaa gaa gct ctt aag tct       2240
Val Asp Lys Pro Thr Ile Gln Phe Ile Val Glu Glu Ala Leu Lys Ser
     35                  40                  45                  50 ggt att gaa gat atc ttg gtt gtt acc ggt aaa tca aaa cgc tct atc       2288
Gly Ile Glu Asp Ile Leu Val Val Thr Gly Lys Ser Lys Arg Ser Ile
                 55                  60                  65 gaa gac cat ttt gac tca aac ttc gaa tta gaa tat aac ttg gaa caa       2336
Glu Asp His Phe Asp Ser Asn Phe Glu Leu Glu Tyr Asn Leu Glu Gln
             70                  75                  80 aaa ggt aag act gac ttg ttg aaa ttg gtt aat gac acc act tct att       2384
Lys Gly Lys Thr Asp Leu Leu Lys Leu Val Asn Asp Thr Thr Ser Ile
         85                  90                  95 aat ctc cac ttt atc cgt caa agt cac cca cgt ggt ctc gga gat gct       2432
Asn Leu His Phe Ile Arg Gln Ser His Pro Arg Gly Leu Gly Asp Ala
    100                 105                 110 gtt ctc caa gcc aaa gca ttt gtc gga aat gaa cct ttt gtt gtc atg       2480
Val Leu Gln Ala Lys Ala Phe Val Gly Asn Glu Pro Phe Val Val Met
115                 120                 125                 130 ctt ggt gac gac ctc atg gat att act aac gac aaa gcg gta cct ttg       2528
Leu Gly Asp Asp Leu Met Asp Ile Thr Asn Asp Lys Ala Val Pro Leu
                135                 140                 145 act aaa caa ctt atc aac gat tat gag gag aca cat gca tct act att       2576
Thr Lys Gln Leu Ile Asn Asp Tyr Glu Glu Thr His Ala Ser Thr Ile
            150                 155                 160
```

```
gcg gtt atg cct gtg tct tct gaa gaa gtc tct gct tat ggt gta atc     2624
Ala Val Met Pro Val Ser Ser Glu Glu Val Ser Ala Tyr Gly Val Ile
        165                 170                 175 gct cct cag ggt aaa ggc gaa aat gga cgt tac agc gtt gaa act ttc     2672
Ala Pro Gln Gly Lys Gly Glu Asn Gly Arg Tyr Ser Val Glu Thr Phe
    180                 185                 190 gtt gaa aaa cca aat cca gaa gat gca ccg agt gat ctt gct atc atc     2720
Val Glu Lys Pro Asn Pro Glu Asp Ala Pro Ser Asp Leu Ala Ile Ile
195                 200                 205                 210 gga cgt tac ctt tta aca cct gag att ttc ggt atc tta gaa aat caa     2768
Gly Arg Tyr Leu Leu Thr Pro Glu Ile Phe Gly Ile Leu Glu Asn Gln
                215                 220                 225 gaa cca ggt gct ggg aat gaa gtc caa ttg act gat gct atc gat act     2816
Glu Pro Gly Ala Gly Asn Glu Val Gln Leu Thr Asp Ala Ile Asp Thr
            230                 235                 240 ctt aac aaa aca caa cgc gtc ttt gct cgt gta ttt aca gga gat cgt     2864
Leu Asn Lys Thr Gln Arg Val Phe Ala Arg Val Phe Thr Gly Asp Arg
        245                 250                 255 tat gat gtc ggt gac aaa ttt ggc ttt atg aag acg tct att gat tac     2912
Tyr Asp Val Gly Asp Lys Phe Gly Phe Met Lys Thr Ser Ile Asp Tyr
    260                 265                 270 gca ctt aaa cac cct caa att aaa gat gac ctt aag caa tac ctt att     2960
Ala Leu Lys His Pro Gln Ile Lys Asp Asp Leu Lys Gln Tyr Leu Ile
275                 280                 285                 290 gaa ttg ggc cac aaa ctt gaa ggc aaa ccc act aaa aaa ggc taa         3005
Glu Leu Gly His Lys Leu Glu Gly Lys Pro Thr Lys Lys Gly
                295                 300                 305 tataaaatcc atcgaatcta atgaacagct ccctgtcaag tggacaatga aataataaaa   3065
tattaggcga cggccttgtt cctcatttca agagggcaa ggccgttatt gcgctcttga    3125
aaacgttgat gattgtaaaa atagatgtag gcatcaatat ctgaaactag ctcctcaaaa   3185
gtcttatact tcttcaaatc atagcactcc gtcttaaagt gcccaaagaa actctcaatt   3245
ggtgcattgt caatacactt accaacacga gacatggagc gggtcatctg atactgggta   3305
gttaaacggt aataatcttt cgaagtatac tgcgaacctc ggtcgctgtg aattaatggt   3365
gtcgcattag ggttagcttt ttgtgcttta cgaagtgttt ccaataccaa ttcgttatca   3425
ttaaattgac caactacata ggcgacaatt gagccgtcgt aaagatcctt aatagcactc   3485
aaataggctt tacagctgaa accgtacttc aagaaagtca catctgtaca ccatttctga   3545
tttggagcag tggctgtaaa attacgattg agaatgttgt cttctacatt gacaaagcta   3605
gttttagtac aatagccctt ggctcttctg ataatggaac gtacacctag aatgtgcatc   3665
aagcgtcgaa tccgcttctt gttgtacttt gtttcaagct tgcgattgac aaatagcgtc   3725
atacgacgat aaccaagaat accattatgc tggctatgaa gtttcttgat gatatccatc   3785
aagcctaaat tttcctgttc agaagttgtt tcttgatgtt gtaaccactt gtaatagcct   3845
gagcgagata cctttagaat atggcacaag tggctgatag aaacctcttc atactcatcc   3905
gcatattctt taatcgcttg gaaggtttcc aagtgccgac caagtcttac cgtcggtttc   3965
gtcgtttgat ttcttctaac ttttttagca ggccgttctc catttcaaga tacttaatcc   4025
gctcttcctg ttgcttgatt ttgaggcgta actcttcttc tggagtaagg tttggtttac   4085
ttgtaagacc ttttccacga cgatctacga gaccgttaga accgtccttc tcgaactttc   4145
tgaccc                                                              4151
```

<210> SEQ ID NO 4
<211> LENGTH: 304

```
<212> TYPE: PRT
<213> ORGANISM: Streptococcus thermophilus

<400> SEQUENCE: 4

Met Lys Asn Gln Lys Val Arg Lys Ala Val Ile Pro Ala Gly Gly Leu
 1               5                  10                  15

Gly Thr Arg Phe Leu Pro Ala Thr Lys Ala Leu Ala Lys Glu Met Phe
                20                  25                  30

Pro Ile Val Asp Lys Pro Thr Ile Gln Phe Ile Val Glu Glu Ala Leu
            35                  40                  45

Lys Ser Gly Ile Glu Asp Ile Leu Val Val Thr Gly Lys Ser Lys Arg
    50                  55                  60

Ser Ile Glu Asp His Phe Asp Ser Asn Phe Glu Leu Glu Tyr Asn Leu
65                  70                  75                  80

Glu Gln Lys Gly Lys Thr Asp Leu Leu Lys Leu Val Asn Asp Thr Thr
                85                  90                  95

Ser Ile Asn Leu His Phe Ile Arg Gln Ser His Pro Arg Gly Leu Gly
                100                 105                 110

Asp Ala Val Leu Gln Ala Lys Ala Phe Val Gly Asn Glu Pro Phe Val
            115                 120                 125

Val Met Leu Gly Asp Asp Leu Met Asp Ile Thr Asn Asp Lys Ala Val
130                 135                 140

Pro Leu Thr Lys Gln Leu Ile Asn Asp Tyr Glu Glu Thr His Ala Ser
145                 150                 155                 160

Thr Ile Ala Val Met Pro Val Ser Ser Glu Val Ser Ala Tyr Gly
                165                 170                 175

Val Ile Ala Pro Gln Gly Lys Gly Glu Asn Gly Arg Tyr Ser Val Glu
            180                 185                 190

Thr Phe Val Glu Lys Pro Asn Pro Glu Asp Ala Pro Ser Asp Leu Ala
        195                 200                 205

Ile Ile Gly Arg Tyr Leu Leu Thr Pro Glu Ile Phe Gly Ile Leu Glu
    210                 215                 220

Asn Gln Glu Pro Gly Ala Gly Asn Glu Val Gln Leu Thr Asp Ala Ile
225                 230                 235                 240

Asp Thr Leu Asn Lys Thr Gln Arg Val Phe Ala Arg Val Phe Thr Gly
                245                 250                 255

Asp Arg Tyr Asp Val Gly Asp Lys Phe Gly Phe Met Lys Thr Ser Ile
            260                 265                 270

Asp Tyr Ala Leu Lys His Pro Gln Ile Lys Asp Asp Leu Lys Gln Tyr
        275                 280                 285

Leu Ile Glu Leu Gly His Lys Leu Glu Gly Lys Pro Thr Lys Lys Gly
    290                 295                 300
```